United States Patent [19]

Eads et al.

[11] Patent Number: 4,660,422

[45] Date of Patent: Apr. 28, 1987

[54] MEANS AND METHOD OF SAMPLING FLOW RELATED VARIABLES FROM A WATERWAY IN AN ACCURATE MANNER USING A PROGRAMMABLE CALCULATOR

[75] Inventors: Rand E. Eads, Eureka; Mark R. Boolootian, Arcata, both of Calif.; Steven C. Hankin, Seattle, Wash.

[73] Assignee: The United States of America as represented by the Secretary of Agriculture, Washington, D.C.

[21] Appl. No.: 825,109

[22] Filed: Feb. 3, 1986

[51] Int. Cl.$^4$ .............................................. G01N 1/44
[52] U.S. Cl. .................................. 73/863.02; 73/291; 73/864.34; 364/581
[58] Field of Search ................ 73/863, 863.01, 864.34, 73/863.02, 863.03, 291, 198, 864.35; 364/581, 178, 179

[56] References Cited

U.S. PATENT DOCUMENTS

| | | | |
|---|---|---|---|
| 3,253,469 | 3/1966 | Norman . | |
| 3,362,222 | 1/1968 | Johnson et al. | 73/198 |
| 3,719,081 | 3/1973 | Lynn et al. | 73/198 |
| 3,727,464 | 4/1973 | Rutkowski et al. | 73/863.01 |
| 3,893,333 | 7/1975 | Sunahara et al. | 73/61 R |
| 3,929,017 | 12/1975 | Kowalski | 73/198 |
| 3,940,993 | 3/1976 | Lapidot . | |
| 4,022,059 | 5/1977 | Schontzks et al. | 73/863.02 X |
| 4,099,871 | 7/1978 | Sunahara et al. | 356/442 X |
| 4,245,758 | 1/1981 | McCabe | 73/198 |
| 4,409,853 | 10/1983 | Chase et al. | 73/863 |
| 4,523,460 | 6/1985 | Strickler et al. | 73/198 X |

FOREIGN PATENT DOCUMENTS 1125493 11/1984 U.S.S.R. ................................ 73/863

OTHER PUBLICATIONS

"Errors in Estimating Suspended Sediment", *Proceedings of the D. B. Simons Symposium on Erosion and Sedimentation*, Sep. 1983, pp. 1.162-1.177, Robert B. Thomas.

"Controlling the Automatic Sampling of Suspended Sediment Using a Programmable Calculator and Interface Circuit", Feb. 1986, Rand E. Eads et al., 33 page draft copy of article published by Forest Service, U.S. Dept. of Agriculture, Arcata, Calif. 95521.

"Estimating Total Suspended Sediment Yield with Probability Sampling", 36 page draft copy of article by Robert B. Thomas, published in Sep. 1986 issue of *Water Resources Research*, vol. 21, No. 9, pp. 1381-1388.

"A Programmable Calculator Improves Automatic Sampling of Suspended Sediment", 16 page draft copy of article by Rand E. Eads et al. to be published in *Water Resources Bulletin* after Feb. 3, 1986.

"An Automatic Sampler for Intermittent Flows of Water", *Instrument Practice*, vol. 8, No. 5, pp. 414-415, May 1954, R. Wilkinson.

"Automated System for Collecting Water Samples in Proportion to Stream Flow Rate", *New Zealand Journal of Science*, vol. 18, No. 2, pp. 289-296, G. G. C. Claridge, Jun. 1975.

*Primary Examiner*—Stewart J. Levy
*Assistant Examiner*—Tom Noland
*Attorney, Agent, or Firm*—M. Howard Silverstein; David G. McConnell

[57] ABSTRACT

A programmable calculator (20) is connected to a pumping sampler (12) by an interface circuit board (22). The calculator has a sediment sampling program stored therein and includes a timer (60) to periodically wake up the calculator. Sediment collection is controlled by a Selection At List Time (SALT) scheme in which the probability of taking a sample is proportional to its estimated contribution to total sediment discharge, or according to accumulated predicted sediment weight. Stage height is also measured and is recorded according to a set scheme.

12 Claims, 2 Drawing Figures

MEANS AND METHOD OF SAMPLING FLOW RELATED VARIABLES FROM A WATERWAY IN AN ACCURATE MANNER USING A PROGRAMMABLE CALCULATOR

TECHNICAL FIELD

The present invention relates generally to determining the amount of sediment in a river or stream. More particularly, the present invention relates to a method of sediment sampling that produces statistically accurate results.

BACKGROUND ART

Knowledge of sediment levels in rivers and streams as well as knowledge of stage height is necessary to accurately determine the effects of logging, industry, land development, or the like on rivers and streams. However, measuring and estimating suspended sediment yields in rivers has long been subject to confusion and uncertainty. Many methods have been developed for collecting data and estimating yields, a fact that suggests the lack of a compelling measurement methodology. The main reason for this situation is the lack of a theoretical framework that defines when discrete samples of suspended sediment should be taken.

The ideal way to estimate the suspended sediment yield of rivers would be to measure suspended sediment discharge continuously. Such data could be integrated over the monitoring period in a way similar to that used to obtain water yield from a discharge hydrograph. There is no technique, however, to monitor suspended sediment discharge directly. A second approach is to measure suspended sediment concentration and water discharge continuously, and use the product function as an estimate of suspended sediment discharge.

Obtaining continuous records of concentration, however, is subject to numerous problems. Such measurements are necessarily indirect; turbidity and water/sediment density are two quantities that can be related to suspended sediment concentration. Calibration of these qualities is a continuing problem, the instrumentation is expensive and subject to breakdown, and 120 volt A.C. electrical power is usually required.

When cost, remoteness of sites, and technical difficulties preclude collecting continuous concentration data, the usual course is to measure water discharge continuously and to take occasional discrete water samples for gravimetric analysis of suspended sediment concentration. The samples are taken manually, or, more commonly in recent years, with automatic sampling equipment.

Automatically pumping samples can facilitate the collection of suspended sediment samples. Most commercial samplers have two operational modes—fixed time intervals and flow-proportional sampling. In most instances, flow-proportional sampling requires an external controller with fixed time intervals handled internally by the sampler.

Pumped suspended sediment samples are often collected at equal intervals of time. This practice produces many samples during low flow conditions and few samples during infrequent high flow conditions. But, reducing the time interval increases the size of the data set with no assurance that high flows will be adequately represented. The need to sample more frequently is often hampered by difficulty of access to remote areas coupled with runoff events of short duration. When dealing with such conditions, long periods of calibration are required, and analyzing streamflow information is delayed because of missing records.

Although numerous methods are available to improve automatic sampling, most rely on a "controller" to skew sampling toward high states or significant events. Several investigators have developed or modified instruments that control the collection of suspended sediment samples. One such instrument is known as a Proportional Frequency Controller and is an electronic device that produces a pulse frequency proportional to water discharge. Sampling frequency is controlled by 34 different stage positions of a float-pulley system. Each position is actuated with a magnetic switch and is adjusted with a fixed and a variable resistor. Consequently, to update a rating equation or move the device to a new location may require a substantial amount of rewiring and calibration. Besides these constraints, moisture and temperature can cause reliability problems. A second system uses a standard water level recorder modified so that the sampling frequency is controlled by switches wired to a timing circuit. Four intervals of stage can be set to five different fixed time intervals ($1\frac{1}{2}$ to 24 hours). Changing time intervals or stage settings requires electronic or mechanical manipulation of the recorder. Another sampling system was developed on the basis of the relationship between rainfall and discharge. Electric pulses from a tipping-bucket rain gauge activated a pumping sampler whenever the rainfall reached a threshold intensity. Sampling continued at regular increments of rainfall until the intensity dropped below the threshold. Thereafter, samples were collected at fixed time intervals.

These methods, although an improvement over fixed time intervals, do not provide for the flexibility to easily change sampling frequencies nor do they produce statistically acceptable data. Therefore, data sets are collected that contain little statistically useful information.

All of these sampling methods are based on the assumption that water height can be related accurately to sediment flow since sampling frequency is altered according to stage height. This assumption is based on prior data concerning a particular waterway. While such assumptions are accurate in a broad sense, they are not accurate enough and therefore affect any data gathered which is based on these data or assumptions.

Therefore, regardless of how the samples are collected, there remain the questions of when the measurements of concentration should be made, how they should be used to estimate the total yield, and what the properties of the estimates are.

In order to overcome these problems, a variety of methods for estimating total suspended yield have been investigated. The tested combinations of estimation technique have ranged from 70% below to 40% above the true value. Most of the estimates were less than 60% of the correct value. The variance of the estimators tended to increase as the accuracy improved, thus cancelling the benefits, and no approach emerged as the ideal choice for all conditions.

These techniques can be termed nonstatistical because the sampling probabilities are not known. The estimators, therefore, cannot take the probability structure into account, resulting in bias (i.e., systematic over- or underestimation of true values) that depends on unknown and variable factors in the data collection process and on specific site conditions. Bias is particularly prevalent when measuring small flashy streams that drain mountainous terrain. In general, higher flows should receive a disportionately large share of sediment sampling effort, but no clear direction has existed to provide either the size of the sample or its distribution over differing flow conditions.

The other major shortcoming of nonstatistical estimators is that they do not allow a valid estimate of precision of the estimated total yields. This fact prevents making valid comparisons between treatments, setting sample size to obtain desired precision of the estimators, and efficient direction of the sampling process.

In this disclosure, "sample size" refers to the number of population units in a statistical sample rather than to the volume of a sample of water used to determine concentration.

Therefore, there is need for a means and method of collecting sediment samples from a stream or river which is based on a sampling strategy which gives estimates with known properties and produces statistically acceptable results and which can be used in association with high flow conditions.

DISCLOSURE OF THE INVENTION

It is a main object of the present invention to obtain accurate data related to the quantity of sediment in a river or stream.

It is another object of the present invention to provide an interface circuit for electrically connecting a programmable calculator to a water stage sensor and a pumping sampler to automatically control the sampler with a stage dependent sampling scheme incorporated in a program in the calculator.

It is another object of the present invention to monitor suspended sediment concentration with variable probability sampling to estimate total suspended sediment yield in a river or stream.

It is another object of the present invention to monitor suspended sediment in a river or stream in a manner which can be changed as desired.

It is another object of the present invention to monitor suspended sediment in a river or stream while also obtaining hydrographic data.

It is another object of the present invention to apply a Selection At List Time (SALT) scheme to control sampling of concentration for estimating total suspended sediment yield.

In this disclosure, "programmable calculator" refers to the HP-41CV, HP-41CX, HP-75C; the words "calculator" and "computer" are used interchangeably and in a general sense.

Three different groups of electronic devices are available to improve sampling efficiency. (1) Commercially available controllers designed for this task are often preprogrammed for a specific site, and generally emphasize data logging instead of handling complex equations; however, system costs can be high. (2) Custom made, microprocessor-based controllers can offer flexibility with moderate component costs. Unfortunately, hardware and software design and development are complex and time-consuming. (3) A programmable calculator capable of controlling pumping samplers allows manipulation of complex equations, flexibility, and is attainable at moderate cost. The use of a programmable calculator permits storage and manipulation of complex equations and relationships at reasonable system cost with reasonable system complexity. Therefore, if a programmable calculator is included in the sediment sampling mechanism, statistically accurate data can be provided. The calculator can be connected to a pumping sampler via the interface circuit, to activate that sampler according to constraints in a program stored in the calculator. The calculator can also store data, such as stage height.

The method used to control sampling is dependent on the techniques of sample survey theory; that is, statistical methods designed for sampling finite populations. The finite population to be sampled and the units that comprise it will be defined, and a sampling method selected to make the best use of the population structure.

The most basic form of probability sampling is called simple random sampling (SRS), where each sample of a given size has the same probability of being selected. Probability sampling, however, does not require that selection probabilities be equal, only that they be known. In many cases, using a strategy that restricts the random selection of sampled units according to relevant population characteristics can reduce sample size or improve precision of the estimators. In this way, other available information can be brought to bear to improve the efficiency of the sampling scheme.

One sampling technique that restricts randomization is termed "sampling with probability proportional to size" (or PPS). "Size" in this context refers to the magnitude of the measured characteristic of the population units. Because these magnitudes are not known until after the sample is collected - and then only for the sampled units - PPS sampling depends on having an easily measured auxiliary variable known to be related to the variables of interest. The auxiliary variable must be easily measurable because it is this variable that defines selection probabilities and therefore must be measured for every unit in the finite population. The auxiliary variable contains outside information that is used to improve the sampling of the primary variable.

A complex relationship is required between the primary and auxiliary variables to make PPS efficient. It is not enough for the variables to simply be correlated. The auxiliary variable must be positively correlated to the square of the primary variable divided by the auxiliary variable. That is, if y is a primary variable, to have x be an effective auxiliary variable requires $\text{Corr}(x, y^2/x) > 0$. The magnitude of this correlation does not affect the unbiasedness of PPS estimators, but stronger correlations reduce the variance of the estimates.

Suppose an investigator wants to estimate the total volume of channel sediments stored in the tributaries of a watershed. If all tributaries cannot be measured, they can be sampled. If SRS is used, all tributaries would have the same chance of entering the sample. With tributaries of widely differing size, however, this approach can be very inefficient. Large tributaries, which contribute heavily to the total, would not be any more likely to enter the sample than small ones, which contribute little.

The investigator would like to preferentially select the important tributaries while still remaining within a well defined probability context. A reasonable auxiliary variable is tributary length which is likely to be related to the volume of stored sediment, and it can easily be measured from maps or photos. The lengths of all tributaries are determined first. The tributaries are listed in any arbitrary order followed by their lengths, and the cumulative sums of the lengths are formed. Suppose n is the desired sample size. Then a set of n uniform random numbers is selected from 0 to the largest cumulative sum. For each random number, the tributary having the next larger cumulative sum is selected for the sample. Because the random numbers are selected uniformly, the probability of selecting any tributary is equal to its length divided by the total of the lengths of all tributaries. The larger tributaries, therefore, have a greater probability of being chosen for the sample. The estimators of total volume of stored sediment and its variance are weighted to account for the unequal—but known— probabilities of selection, making both statistics unbiased.

While this scheme will work well for many problems, it does require that all values of the auxiliary variable be known before sampling of the primary variable can begin. This requires two traverses of the population, one to measure the auxiliary variable values of all units, and one to measure the primary variable on those units selected for the sample. This procedure will not work, therefore, when sampling a time dependent process such as suspended sediment. Any auxiliary variable would have to depend on conditions during the measurement period, at which time it would be too late to sample.

An improved PPS sampling technique was developed to avoid this general problem and adapted to sampling forest tree volume. A further refinement, also developed for forestry use, is called SALT (Selection At List Time) sampling. SALT sampling provides a technique for creating a list of random numbers before the time period being monitored, and for using these numbers to determine which units should be sampled as the auxiliary variable values become available during the process. The SALT estimators give unbiased estimates of the total and its variance.

Using pumping samplers, small battery-powered computers, and stage sensing devices at gauging stations offers an opportunity to employ probability sampling to monitor sediment and estimate suspended sediment yield more efficiently. The selection at list time (SALT) technique for sampling sediment with probability proportional to the magnitude of estimated sediment transport employs a sediment rating function to calculate an auxiliary variable that directs the sampling process. The auxiliary variable is an estimate of the suspended sediment yield during a short time period (sample unit), and must be calculated for every unit in the population. Sampling efficiency is improved because the probability of taking a sample is proportional to the estimated contribution of that unit to the total yield. Sample size is set to obtain estimates with desired performance. This sampling scheme gives unbiased estimates of suspended sediment yield and its variance and requires fewer field measurements than commonly used techniques. It automatically emphasizes concentration sampling at higher flow levels by using presently available technology.

Therefore, the present invention provides a means and method for connecting a programmable calculator to a stage sensing device and a pumping sampler, and programs the SALT scheme or another appropriate scheme into that calculator to control the sampling of suspended sediment concentration in a river or stream.

DETAILED DESCRIPTION OF THE BEST MODE FOR CARRYING OUT THE INVENTION

Figure 1:
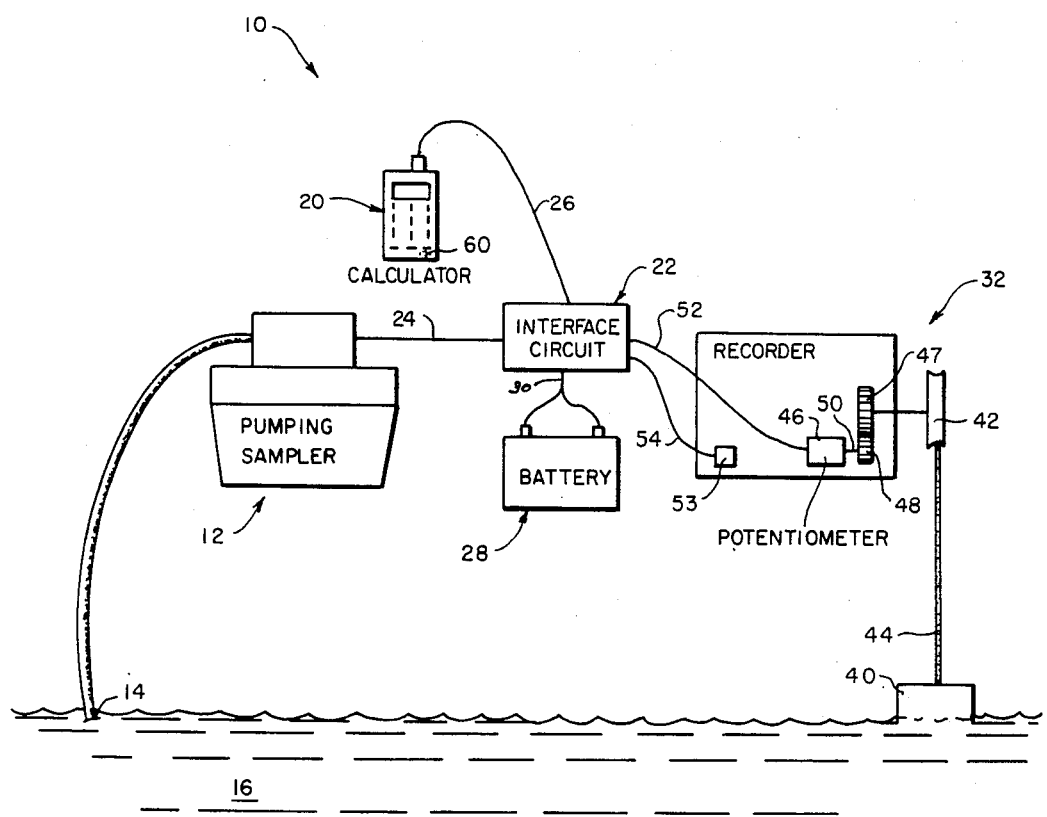
FIG. 1 is a schematic representation of the equipment used to effect stage controlled collection of suspended sediment samples.

Shown in FIG. 1 is a sediment sampling means 10 which is used to collect sediment samples from a river or a stream according to a SALT scheme. The sampling means 10 includes a pumping sampler 12 having an intake 14 immersed in a waterway 16 for withdrawing sediment samples and transferring those samples to a suitable storage means. The collected sediment samples can be analyzed to obtain suspended sediment concentration.

Operation of the pumping sampler is controlled by a programmable calculator 20 via an interface circuit board 22 and leads 24 and 26 respectively. The circuit board is coupled to a power source 28 by suitable leads 30. The interface circuit board 22 also supplies power to the stage height measuring means 32 which measures the height of the waterway 16 and records that measurement for back up records. The stage height measuring means converts water stage from mechanical to electrical information and includes a float 40 coupled to a pulley 42 by a float tape 44. The pulley 42 is attached to a potentiometer 46 by meshed gears 47 and 48 and shaft 50. The output of the potentiometer varies according to the height of float 40 and the potentiometer output is supplied to the interface circuit board by a lead 52. The interface circuit is connected to an event marker 53 which is used for backup pumped sample records via a lead 54. The analog output signal from the potentiometer is converted to a digital signal by the interface circuit and transmitted to the computer for use by the sampling program. The memory can be transferred to magnetic tape at suitable times and electronically transferred to an office computer for storage and analysis.

The pumping sampler 12 and the stage height measuring means 32 are known and the structural details of these elements per se do not form part of this invention.

Figure 2:
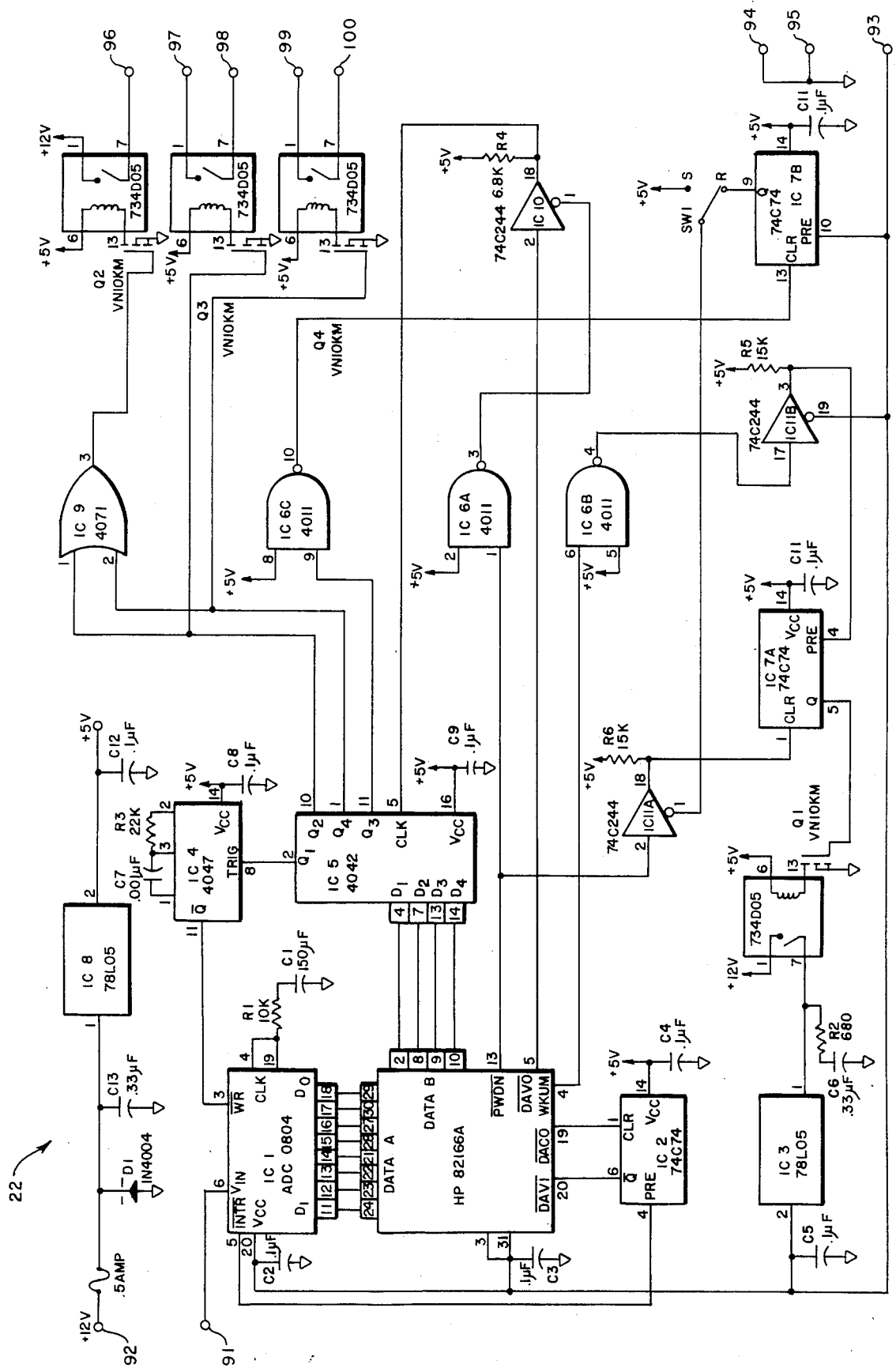
FIG. 2 is a schematic of a circuit board used to interface a programmable calculator to a stage sensing device and to a pumping sampler.

The calculator itself can be any of at least four well known elements: the HP-75 (TM of the Hewlett-Packard Co.), or the HP-71 (TM of Hewlett-Packard Co.), or the HP-41CV, or HP-41CX, the details of which are not part of the invention. It is the use, itself, of a programmable calculator in a sediment sampling setup that forms an important part of the present invention, not the calculator itself. An HP-IL (TM of Hewlett-Packard Co.) interface module can be used to provide a physical two-wire link between the calculator and the interface circuit board. A schematic of the interface circuit board 22 is shown in FIG. 2, and a complete description of the calculator and circuit board are disclosed in "Controlling the Automatic Sampling of Suspended Sediment Using a Programmable Calculator and Interface Circuit", also known as "Controlling Suspended Sediment Samplers by Programmable Calculator and Interface Circuitry", by Rand E. Eads and Mark R. Boolootian of Pacific Southwest Forest and Range Experiment Station and published by the Forest Service, U.S. Department of Agriculture, Arcata, Calif. 95521.

However, in the interest of clarity, the circuit will be briefly described. Referring to FIG. 2, the circuit includes a lead 91 which connects potentiometer 46 to a voltage source (not shown), while the system is attached to power source 28 via lead 30 and connection 92. Voltage of potentiometer 46 is applied via lead connection 93 and is used in the production of an analog signal representing water level. Connecting leads 94 and 95 are system grounds attached to power source 28 via lead 30. Voltage is applied to the event marker 53 via lead connection 96, while lead connections 97 and 98 are relay connections to pumping sampler 12 via lead 24. Lead connections 99 and 100 connect the system to another sampler (not shown).

The use of the sampling means 10 is discussed in "A Programmable Calculator Improves Automatic Sampling of Suspended Sediment" by Rand E. Eads, Steven C. Hankin and Mark R. Boolootian of Pacific Southwest Forest and Range Experiment Station, which has been completed and is awaiting publication in Water Resources Bulletin.

The present invention includes implementing the SALT scheme to control sampling of concentration for estimating total suspended sediment yield. This implementing is fully disclosed and discussed in "Estimating Total Suspended Sediment Yield with Probability Sampling", by Robert B. Thomas of the Pacific Southwest Forest and Range Experiment Station of the U. S. Forest Service, and in press for Water Resources Bulletin. Thus, the SALT scheme and its application to the sampling of suspended sediment will only be disclosed sufficiently to understand the present invention. The full details are available in the referenced Thomas Paper. The calculator has a time element 60 programmed to turn that calculator on and off at predetermined times. The calculator is off most of the time to conserve the batteries and wakes up at specified periods to execute the sampling program. The wake-up periods are close enough together that adequate states in the river or stream are sampled, even during rapidly rising stages. A preferred wake-up period is ten minutes.

Several ideas must be developed to apply the SALT technique to estimating suspended sediment yields. The first of these is the definition of the finite population and the units that comprise it. The population must be composed of units that are non-overlapping, exhaustive, and well defined for selection purposes. "Short" periods of time define the population units, and a measure of suspended sediment yield during the period is the characteristic of interest. A common duration (e.g., 5 to 30 minutes) must be chosen for the sampling periods for a given time period to be monitored. Let $y_i$ be the *measure* of suspended sediment yield for the $i^{th}$ time period (i.e., population unit). Then, $$y_i = q_i c_i \Delta t\, K,$$

where $q_i$ is the water discharge rate and $c_i$ is the suspended sediment concentration for the $i^{th}$ period, $\Delta t$ is the time duration chosen for the sampling periods, and K is a constant to convert units. For example, if $q_i$ is in m³/s, $c_i$ is in mg/l, and the sampling period is 1800 seconds (i.e., 30 minutes), then $K = 10^{-3}(1 \cdot kg)/(m^3 \cdot mg)$ gives $y_i$ in kg.

If the sampling period duration is short enough we can use the water discharge rate at the midpoint of the period for $q_i$. In a similar way, $c_i$ will be a discrete sample of suspended sediment concentration taken at the midpoint usually with a pumping sampler. A sampling unit, therefore, is represented by the conditions at the midpoint of the sampling period. This means that the "sampled population" (i.e., the population of $y_i$'s) is not identical to the "target population" consisting of the continuous records. By adjusting the sampling period duration, however, these two populations can be made to match as closely as desired.

The sampled population, therefore, consists of all of the $y_i$'s for the period being monitored. If resources were adequate all of the values of $y_i$ could be measured to determine the total suspended yield. That is, if there are N sampling periods in the monitoring period, the "true" population total, Y, is given by $$Y = \sum_{i=1}^{N} y_i$$

It henceforth will be assumed that the sampling period duration has been chosen to satisfy the hydrologist that the target and sampled populations are sufficiently similar for the investigation in question.

An auxiliary variable that can be measured throughout the period being monitored is required to perform SALT sampling on this population. Because water discharge is usually measured continuously, an ideal auxiliary variable is the common sediment rating function that expresses suspended sediment concentration as a function of the rate of water discharge. Let f be this empirically determined function and $\hat{c}_i$ denote the estimated concentration. Then, $$\hat{c}_i = f(q_i)$$

is an estimate of the suspended sediment concentration at the midpoint of the $i^{th}$ interval We can now define $x_i$ as an *estimate* of the suspended sediment dischrage for the $i^{th}$ sampling period. That is, $$x_i = q_i \hat{c}_i \Delta t\, K,$$

which is identical to the formula for $y_i$ except that $c_i$ has been replaced by $\hat{c}_i$.

The value of $x_i$ will be known for every sampling period in the period to be monitored. Therefore, the total estimated suspended sediment yield, X, can be defined as, $$X = \sum_{i=1}^{N} x_i .$$

There is a problem of having to know f before sampling can begin, but having to sample before f can be determined. In many basins, some sediment rating data will exist that can be used to make at least preliminary estimates of the rating function. These estimates can be revised as SALT data accumulate. As a last resort, data from nearby catchments can be used for tentative estimates until data from the monitored stream become available. The quality of f does not affect the unbiasedness of the estimator of suspended yield, but it does affect its variance. That is, the better f predicts $c_i$, the lower the variance of the estimate of the yield.

Preparing for Sampling

Accomplishing the SALT process in "real time" generally requires additional instrumentation at a gauging station. SALT sampling will usually be used at a station that has a continuous stage recorder and a pumping sampler. Sampling periods should be "short"—especially on streams having highly variable suspended sediment concentrations—so determination of $x_i$ will have to be done frequently. This is accomplished by sediment sampling means 10.

A set of random numbers must be selected before sampling each period to be monitored. This is done by making a preliminary estimate, Y', of Y, the total suspended sediment yield expected during the period to be monitored. To insure that the random numbers cover a sufficiently large range to sample the expected yield of suspended sediment, Y' is multiplied by a factor, W, to obtain:

$$Y^* = W\ Y'.$$

W is essentially a factor of safety ensuring a near zero probability that the total estimated suspended sediment yield, X, is greater than $Y^*$. If X exceeds $Y^*$ the sampling algorithm will run out of random numbers. The magnitude of W will reflect the quality of existing data and the consequent uncertainty of the estimate, Y', but it will usually be in the range from 2 to 10.

A procedure is described in the incorporated by reference Thomas paper to establish $n^*$, the number of random numbers that must be preselected to obtain a specified level of performance for the estimators. Assuming temporarily that its value is known, $n^*$ uniform random numbers are selected from the interval $(0, Y^*]$, where the parenthesis indicates exclusion of the boundary point from the interval, and the square bracket indicates inclusion. The actual selection is carried out in the calculator using a pseudorandom number generator. The random numbers are sorted into ascending order (to facilitate their use during sampling) and stored in the computer.

The SALT sampling process and the procedure for estimating total suspended sediment yield are fully described in the referenced Thomas paper, and attention is directed thereto for such disclosure. A procedure for establishing sample size is also described in that paper. Data are retrieved from the calculator by a portable digital cassette recorder and can be transferred to a computer without intermediate reduction or manual entry.

INDUSTRIAL APPLICABILITY

While the SALT scheme has been described as the means for controlling the sampling process, other schemes are also available due to the versatility of the programmable calculator. Another effective control scheme includes basing the sampling on the estimated suspended sediment yield. In such a scheme, each time the calculator wakes up it measures the stage height and estimates the sediment yield based on past sediment vs. stage height relationships for the particular waterway being monitored. This predicted value is stored in memory. Each new predicted value is added to the predicted value already stored in the memory. When the summation of predicted yield values exceeds a preselected level, a water/sediment sample is collected. In this manner, the sampling procedure is controlled by the estimated amount of suspended sediment passing the monitoring station. Other sediment sampling methods can also be used by altering the program in the calculator accordingly.

If no rating data exist for the waterway of interest, temporary equations can be constructed from a similar watershed. As rating data are developed, the program is modified to reflect any changes, and changed as frequently as every storm event, if desired.

While the wake-up period has been disclosed as being ten minutes, other intervals can be used.

The calculator can also be used to accumulate hydrographic data. For example, every time the calculator wakes up, stage height is measured, if the just-measured stage height corresponds to that height which is predicted within a stated tolerance by a straight line extrapolation of the last two stored measurements, the just-measured value is not stored. However, if the just-measured value deviates from the predicted value by more than the tolerance, the just-measured value is stored and used to modify the straight line extrapolation.

We claim:

1. A method of controlling the sampling of flow related variables from a waterway which has various stages including steps of:
    obtaining a sample from the waterway with a pumping sampler;
    sensing the stage of the waterway with a water stage sensor;
    providing a programmable calculator;
    providing an interface circuit board to electronically connect said programmable calculator to said pumping sampler and to said water stage sensor; and
    using a SALT scheme to automatically control when a sample is taken from the waterway.

2. The method defined in claim 1 wherein the flow-related variables include the level of suspended sediment.

3. The method defined in claim 2 further including a step of comparing the sensed stage of the waterway to a predicted value of stage height.

4. The method defined in claim 3 further including a step of recording the sensed stage height of that sensed stage height differing from the predicted stage height by more than a predetermined value.

5. A method of controlling the sampling of sediment from a waterway including steps of:
    providing a pumping sampler for sample collection from the waterway;
    providing a water stage sensor for sensing the stage of the waterway;
    providing a programmable calculator;
    providing an interface circuit board to electrically connect said programmable calculator to said pumping sampler and to said water stage sensor;
    and automatically controlling when a sample is taken from the waterway by measuring stage height of the waterway with said water stage sensor,
    predicting the amount of sediment which corresponds to that stage height with said programmable calculator,
    recording a value which corresponds to the amount of sediment predicted, and
    collecting the sample of sediment when the recorded value reaches a predetermined value with said pumping sampler.

6. The method defined in claim 5 including measuring stage height and predicting the amount of sediment a plurality of times and further including a step of adding the predicted values together to define an accumulated sediment value and then collecting a sediment sample when that accumulated sediment value reaches the predetermined value.

7. The method defined in claim 5 wherein said measuring and predicting steps are carried out periodically on a set period which is independent on stage height.

8. A means for sampling sediment from a waterway comprising:
   a pumping sampler means for withdrawing water/sediment from the waterway;
   a programmable calculator means for controlling said pumping sampler, said programmable calculator means including means for activating said pumping sampler according to a SALT sampling scheme;
   recording means for recording stage height; and
   interface circuit board means connecting said programmable calculator to said pumping sampler means and to said recording means.

9. A means for sampling sediment from a waterway comprising:
   (a) a pumping sampler means for withdrawing water/sediment from the waterway;
   (b) measuring means for measuring the stage of said waterway;
   (c) a programmable calculator means for controlling said pumping sampler, said programmable calculator including
      (1) means for predicting the amount of sediment for the stage measured by said measuring means, and
      (2) means for activating said pumping sampler means when the predicted amount of sediment reaches a predetermined value; and
   (d) interface circuit board means connecting said programmable calculator to said pumping sampler means and to said measuring means.

10. The means defined in claim 9 wherein a plurality of stage measurements are made and wherein a corresponding plurality of sediment values are predicted by said programmable calculator, and said programmable calculator further includes means for summing said plurality of predicted sediment values and activating said pumping sampler means where said sum of predicted values exceeds a predetermined value.

11. The means defined in claim 9 wherein said programmable calculator further includes means for recording height of the water in the waterway.

12. The means defined in claim 11 wherein said programmable calculator further includes means for activating said programmable calculator at periodic intervals which are independent of stage height.

* * * * *